(12) United States Patent
Qiang et al.

(10) Patent No.: US 9,468,209 B2
(45) Date of Patent: *Oct. 18, 2016

(54) METHOD FOR ERADICATING WEEDS WITH DERIVATIVES OF 3-ACETYL-5-SEC-BUTYL-4-HYDROXY-3-PYRROLIN-2-ONE

(71) Applicant: Nanjing Agricultural University, Nanjing (CN)

(72) Inventors: Sheng Qiang, Nanjing (CN); Shiguo Chen, Nanjing (CN); Chunlong Yang, Nanjing (CN); Xinbin Dai, Nanjing (CN); Yunfa Dong, Nanjing (CN)

(73) Assignee: NANJING AGRICULTURAL UNIVERSITY, Nanjing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/548,289

(22) Filed: Nov. 20, 2014

(65) Prior Publication Data

US 2015/0141254 A1    May 21, 2015

Related U.S. Application Data

(62) Division of application No. 13/414,711, filed on Mar. 7, 2012, now Pat. No. 8,921,274.

(51) Int. Cl.
*A01N 43/36* (2006.01)
*C07D 207/38* (2006.01)

(52) U.S. Cl.
CPC ............. *A01N 43/36* (2013.01); *C07D 207/38* (2013.01)

(58) Field of Classification Search
CPC ............................ A01N 43/36; C07D 207/38
See application file for complete search history.

(56) References Cited

U.S. PATENT DOCUMENTS 5,008,402 A * 4/1991 Meul .................... C07D 207/38
548/544
8,921,274 B2 * 12/2014 Qiang et al. ......... C07D 207/38
504/283

OTHER PUBLICATIONS

Meul et al (1990): STN International HCAPLUS database, (Columbus, Ohio), Accession No. 1990:515075.*
La Croix et al (1976): STN International HCAPLUS database, (Columbus, Ohio), Accession No. 1976: 131414.*
Harris et al (1965): STN International HCAPLUS database, (Columbus, Ohio), Accession No. 1965: 423983.*

* cited by examiner

*Primary Examiner* — Golam M M Shameem
(74) *Attorney, Agent, or Firm* — Kening Li; Miller Carfield

(57) ABSTRACT

A compound represented by formula (I), or (II), or a salt thereof, for eradicating weeds.

8 Claims, No Drawings

METHOD FOR ERADICATING WEEDS WITH DERIVATIVES OF 3-ACETYL-5-SEC-BUTYL-4-HYDROXY-3-PYRROLIN-2-ONE

CROSS-PREFERENCE TO RELATED APPLICATIONS

This application is a divisional application of U.S. Ser. No. 13/414,711 filed on Mar. 7, 2012.

Ser. No. 13/414,711 is a divisional of U.S. Ser. No. 12/055,384 filed on Mar. 26, 2008, which is a continuation of International Patent Application No. PCT/CN2006/001315 with an international filing date of Jun. 13, 2006, designating the United States, and further claims foreign priority benefits to Chinese Patent Application No. 200510094521.9 filed Sep. 26, 2005. The contents of all of the aforementioned specifications are incorporated herein by reference in their entirety.

BACKGROUND OF THE INVENTION

1. Field of Invention

This invention relates to a method for eradicating weeds using pyrrolidineone derivatives of herbicidal tenuazonic acid (3-acetyl-5-sec-butyl-4-hydroxy-3-pyrrolin-2-one).

2. Description of the Related Art

Tenuazonic acid (formula name 3-acetyl-5-sec-butyl-4-hydroxy-3-pyrrolin-2-one) is a strong phytotoxin isolated, purified, and identified from metabolites of *Alternaria Alternata* by Qiang Sheng et al. It is isolated from a crude mixture of metabolites by the extraction of the fermentation fluid. Due to the low yield (0.0005%) and high cost of fermentation, it is very urgent to develop a synthetic process of the compound.

3-Acetyl-4-hydroxy-5-tert-butylpyrroline-2-ketone is a heterocyclic compound containing carbonyl and hydroxyl functional groups. The lactam that is a part of the heterocyclic ring is the most important functional group. The hydrophobic side chain also plays an important role in its herbicidal activity.

The compound is very effective at killing monocotyledon weeds (such as common crabgrass and barnyardgrass) and dicotyledonous weeds including Crofton weeds at a concentration of 50 μg/mL. It has the potential to become a biological herbicide (CN Pat. Appl. No. 200510038263.2; CN Pat. No. 1644046). However, the low yield and high cost associated with the fermentation process prevents large-scale production of this compound.

A patent (WO1994/01401) discloses 3-benzoylpyrrolidine-2,4-dione derivatives and their herbicidal activity.

CN. Pat. Pub. No. 1676515A made claims based on the fact that some triketones inhibit 4-hydroxyphenylpyruvate dioxygenase (HPPD), which is a key enzyme responsible for biosynthesis of plastoquinone and α-tocopherol. If the biosynthesis of plastoquinone and C-tocopherol is blocked, it will impact the biosynthesis of carotenoids. Therefore, HPPD inhibitor and carotenoid inhibitors have similar functions. This type of compounds has similar structural modification and synthesis, i.e., the existence of N-substituent. The major representative of this type of herbicides is sulfentrazone, isoxazole herbicide, and pyridine type herbicides. It is reported that tenuazonic acid copper salt has a slight inhibition to HPPD (Meazza et al., 2002). With only hydrogen attached to nitrogen, no other substituents, it is obvious that 3-acetyl-4-hydroxy-5-tert-butylpyrroline-2-ketone has a totally different mechanism of action.

Study on the mechanism of action of 3-acetyl-4-hydroxy-5-tert-butylpyrroline 2-ketone has shown that the phytotoxin clearly inhibits the photosynthesis of plants. Its inhibition to Hill reaction is much higher than the typical photosynthetic inhibitor (herbicide), such as 3-(3,4-dichlorophenyl)-1,1-dimethylurea (DCMU). In addition, there is no adverse effect to other parts of the cells. The compound blocks electron flow from $Q_A$ to $Q_B$ in the photosystem II, but has no effect on the donor of photosystem II, photosystem I and other parts of chloroplasts, which was the first time such effects were observed among known phytotoxins produced by fungus *Alternaria alternata*.

It is believed that the toxin interacts with D1 protein by competing with $Q_B$ for the binding site and thus inhibits the electron transfer. Therefore, it is an inhibitory phytotoxin of photosystem II. Based on the discovery of this mechanism, the molecular structure of tenuazonic acid has heretofore been modified to yield a series of new herbicidal molecules (See CN Appl. Nos. 200510094521.9 and 200610038765.X, and CN Pat Pub No. CN1752075).

Many photosystem II inhibitors have successfully become commercial herbicides in the field of herbicides, such as s-triazines, triazinones and phenols, etc. There are two advantages associated with the photosystem II inhibitors: first, since photosynthesis is a common phenomenon among plants, and inhibition is specific to the plants, the toxicity to animals is low, thus this type of herbicides possesses the characteristics of high efficacy and low toxicity. Second, with the development of transgenic technology, there are 67,700,000 hectares of farm land that grow transgenic crops globally and greater than 80% of these crops are herbicide-resistant transgenic (based on Monsanto's 2003 data).

The photosynthetic inhibitors herbicides have a growing share of the herbicides market. With combination of new herbicides and transgenic agricultural products, the chemical pollution to the environment has been greatly reduced. Since the photosynthetic inhibition is the only effect for 3-acetyl-5-sec-butyl-4-hydroxy-3-pyrrolin-2-one on the plant cells, this type of herbicide with high potency, quick action, broad-spectrum, simple structure, and easy synthesis will have a bright future.

There are many types of photosystem II inhibitors according to their chemical structures such as ureas, pyridines, triazinones, pyridazinones, dinitrophenols and cyanophenols, etc. They can be divided into two main groups such as ureas/triazine and phenol. The first type (classical photosystem II inhibitors) can be represented as N—C=X (X stands for O or N atom, not sulfur atom), i.e. atrazine, metribuzin, phemedipham, terbutryand, N-(3,4-dichlorophenyl)-N'-methylurea (DCMU) et al. The second type is phenolic herbicide, including ioxynil, dinoseb and 2-iodo-4-nitro-6-isobutylphenol, etc.

The common feature of the second type of herbicide is that the molecules contain at least one carbonyl oxygen or hydroxy oxygen and a long hydrophobic hydrocarbon side-chain. Most of these herbicides form a hydrogen bond between the carbonyl hydrogen and the D1 protein of photosystem II, which enables them to successfully compete with plastoquinone $Q_B$ (secondary electron acceptor), thereby blocking electron transfer from $Q_A$ to $Q_B$ and leading to the inhibition of photosynthetic process of the plant.

Only a small number of herbicides form hydrogen bond between hydroxyl oxygen and D1 protein and successfully block photosynthetic process. The structure of the hydrophobic hydrocarbon side-chain (number of carbon and chain length) also influences herbicidal activity. Obviously, the binding site, binding manner, and possible binding region of herbicides to D1 protein determine the strength of herbicidal activity. Based on the chemical structure, 3-acetyl-5-sec-butyl-4-hydroxy-3-pyrrolin-2-one belongs to the group of photosystem II inhibitor (containing N—C=O). Unlike the classical herbicides mentioned above, there are no literatures that describe the mechanism of action of this compound to photosynthesis. Therefore, it might be a new type of photosystem II inhibitor.

3-acetyl-5-sec-butyl-4-hydroxy-3-pyrrolin-2-one has moderate toxicity of 200 mg/kg to rat and moderate level phytotoxicity, which is acceptable in light of its high biological activity. However, its toxicity level may be reduced through modification of its chemical structure.

SUMMARY OF THE INVENTION

In one embodiment, the invention provides compounds represented by the general formula (I), or (II), or a salt thereof,

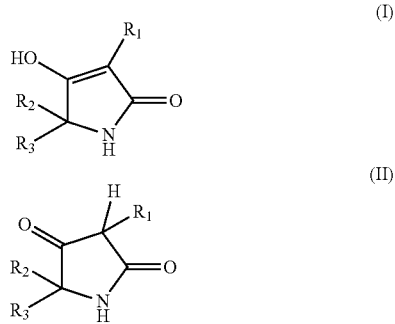

wherein, $R_1$ independently and at each occurrence represents H; or —$C_kH_{2k+1}$, —$OC_kH_{2k+1}$, —(C=O)$C_kH_{2k+1}$, —COOC$_kH_{2k+1}$, —$C_kH_{2k-1}$, —$OC_kH_{2k-1}$, —(C=O)$C_kH_{2k-1}$, or —COOC$_kH_{2k-1}$, each unsubstituted or substituted by one or more substituents selected from a heterocycle, an aryl, a phenylalkyl, a heterocycloalkyl phenyl, a heterocycloalkyl, a heterocycloalkoxyl, a phenoxyl; a phenoxy phenyl; a halogen, a cyano, a nitro, an alkoxyalkyl, an alkoxycarbonyl, and/or an amido.

In a class of this embodiment, $R_2$ and $R_3$ independently and at each occurrence represent H, $C_nH_{2n+1}$, $C_nH_{2n-1}$, a halogen, —CN, a phenyl, a halogenated alkyl, a cyanoalkyl, a phenylalkyl, a halogenoalkenyl, a cyanoalkenyl, or a phenylalkenyl.

In another class of this embodiment, $R_2$ and $R_3$ independently and at each occurrence represent H, —$CH_3$, —$C_2H_5$, —$CH_2CH_2CH_3$, —$CH(CH_3)_2$, —$(CH_2)_3CH_3$, —$C(CH_3)_3$, —$CH_2CH(CH_3)CH_3$, —$CH(CH_3)CH_2CH_3$, —$(CH_2)_4CH_3$, —$CH(CH_3)CH_2CH_2CH_3$, —$CH_2CH(CH_3)CH_2CH_3$, —$CH_2CH_2CH(CH_3)_2$, —$CH(CH_2CH_3)_2$, —$C(CH_2)_2C_2H_5$, —$(CH_2)_5CH_3$, —$CH(CH_3)(CH_2)_3CH_3$, —$CH_2CH(CH_3)(CH_2)_2CH_3$, —$CH_2CH_2CH(CH_3)CH_2CH_3$, —$(CH_2)_3CH(CH_3)_2$, —$CH(CH_2CH_3)CH_2CH_2CH_3$, —$CH_2CH(CH_2CH_3)_2$, —$C(CH_3)_2(CH_2)_2CH_3$, —$C(CH_3)CH_2CH_3)_2$, —$(CH_2)CH_3$, —$CH(CH_2CH_2CH_3)_2$, —$CH_2CH_2CH(CH_2CH_3)_2$, —$CH(CH_2CH_3)(CH_2)_3CH_3$, —$CH_2CH(CH_2CH_3)CH_2CH_2CH_3$, —$CH(CH_3)(CH_2)_4CH_3$, —$CH_2CH(CH_3)(CH_2)_3CH_3$, —$(CH_2)_2CH(CH_3)(CH_2)_2CH_3$, —$(CH_2)_3CH(CH_3)CH_2CH_3$, —$(CH_2)_7CH_3$, —$CH(CH_2CH_2CH_2CH_3)_2$, —$CH(CH_2CH_2CH_3)(CH_2)_3CH_3$, —$CH(CH_3)_5CH_3$, —$CH_2CH(CH_3)(CH_2)_4CH_3$, —$(CH_2)_2CH(CH_3)(CH_2)_3CH_3$, —$(CH_2)_3CH(CH_3)(CH_2)_2CH_3$, —$(CH_2)_4CH(CH_3)CH_2CH_3$, —$(CH_2)_3CH(CH_2CH_3)_2$, —$CH_2CH(CH_2CH_3)(CH_2)_3CH_3$, —$(CH_2)_2CH(CH_2CH_3)(CH_2)_2CH_3$, —$CH=CH_2$, —$CH=CHCH_3$, —$CH_2CH=CH_2$, —$CH=CHCH_2CH_3$, —$CH_2CH_2CH=CH_2$, —$CH_2CH=CHCH_3$, or —$CH=CH—CH=CH_2$.

In another class of this embodiment, $R_2$ and $R_3$ independently and at each occurrence represent —ON or a phenyl group substituted at positions 1-3 by a substituent selected from: —$CHClCH_3$, —$CHClCH_2CH_3$, —$CHClC_3H_7$, —$CHClC_4H_9$, —$CHClC_5H_{11}$, —$CHClC_6H_{13}$, —$CHClC_7H_{15}$, —$CHFCH_3$, —$CHFCH_2CH_3$, —$CHFC_3H_7$, —$CHFC_4H_9$, —$CHFC_5H_{11}$, —$CHFC_6H_{13}$, —$CHFC_7H_{15}$, —$CHCNCH_3$, —$CHCNCH_2CH_3$, —$CHCNC_3H_7$, —$CHCNC_4H_9$, —$CHCNC_5H_{11}$, —$CHCNC_6H_{13}$, —$CHCNC_7H_{15}$, —$CH(C_6H_5)CH_3$, —$CH(C_6H_5)CH_2CH_3$, —$CH(C_6H_5)C_3H_7$, —$CH(C_6H_5)C_4H_9$, —$CH(C_6H_5)C_5H_{11}$, —$CH(C_6H_5)C_6H_{13}$, —$CH(C_6H_5)C_7H_{15}$, —$CHClCH=CH_2$, —$CHClCH_2CH=CH_2$, or a corresponding isomeric halogenate.

In another class of this embodiment, X is CN, a $C_1$ to $C_5$ amido, a benzyl, a naphthalenyl, a phenyl, a pyrrolyl, a furyl, a thiazolyl, a heterocyclic alkyl phenyl; each phenyl or heterocycle being unsubstituted or substituted by a substituent selected from a $C_1$ to $C_6$ alkyl, a $C_1$ to $C_4$ alkoxy, a halogenated $C_1$ to $C_5$ alkyl, a halogen, a $C_1$ to $C_5$ amido, a nitro, a cyano, an alkoxycarbonyl, and/or a $C_1$ to $C_5$ sulfonyl group.

In another class of this embodiment, the compounds are calcium, magnesium, copper, iron, nickel, sodium, potassium, magnesium, zinc or ammonium salts.

In another class of this embodiment, k represents an integer from 1 to 8.

In another class of this embodiment, n represent an integer from 1 to 15.

In another embodiment, the invention is directed to compounds represented by the general formula (II), (IV), or (V)

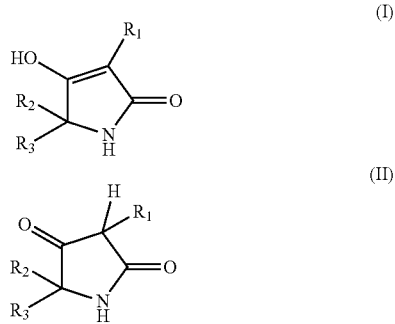

In a class of this embodiment, X independently and at each occurrence represents H; or —$C_mH_{2m+1}$, or —$OC_mH_{2m+1}$, each unsubstituted or substituted by one or more substituents selected from a heterocyclic alkyl, a heterocyclic aryl, an aryl, a phenylalkyl, a heterocycloalkyl phenyl, a heterocycloalkyl, a heterocycloalkoxyl, a phenoxyl; a phenoxy phenyl; a halogen, a cyano, a nitro, an alkoxyalkyl, an alkoxycarbonyl, and/or an amido.

In another class of this embodiment, $R_2$ and $R_3$ independently and at each occurrence represents H, $C_nH_{2+1}$, $C_nH_{2-1}$, a halogen, —CN, a phenyl, a halogenated alkyl, a cyanoalkyl, a phenylalkyl, a halogenoalkenyl, a cyanoalkenyl, or a phenylalkenyl.

In another class of this embodiment, m represents an integer from 1 to 7.

In another aspect, the invention is directed to a method for preparation of a compound comprising the following steps:
a) reacting an amino acid of formula:

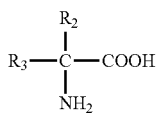

with an alcohol under acidic reaction conditions;
b) neutralizing with sodium ethoxide; and
c) adding a compound of formula $XCOCH_2COY$ or cyclobutane-1,3-dione in the presence of a sodium alkoxide.

In a class of this embodiment, X independently and at each occurrence represents H; or —$C_mH_{2m+1}$, or —$OC_mH_{2m+1}$, each unsubstituted or substituted by one or more substituents selected from a heterocyclic alkyl, a heterocyclic aryl, an aryl, a phenylalkyl, a heterocycloalkyl phenyl, a heterocycloalkyl, a heterocycloalkoxyl, a phenoxyl; a phenoxy phenyl; a halogen, a cyano, a nitro, an alkoxyalkyl, an alkoxycarbonyl, and/or an amido.

In another class of this embodiment, m represents an integer from 1 to 7.

In another class of this embodiment, Y is Cl or Br.

In another class of this embodiment, the steps are carried out in situ without purification of intermediates.

In another aspect, the invention is directed to a method of eradicating weeds, comprising applying to the weeds compounds described herein.

In a class of this embodiment, the compound is applied in a solution having a concentration of between 10 and 800 μg of the compound per 1 g of the solution.

In another class of this embodiment, the weeds are broadleaf plants, grassy weeds, or sedge weeds.

In another class of this embodiment, the compound is applied under exposure to sun light.

In another class of this embodiment, the compound inhibits photosynthesis and metabolism of the plant cell, which causes a rapid accumulation of large amounts of reactive oxygen species in cells of the weeds and subsequent death of the cells.

This invention provides a pyrolidineone-type herbicide, which was developed through a modification of tenuazonic acid, a patented herbicidal compound (chemical name: 3-acetyl-5-sec-butyl-4-hydroxy-3-pyrrolin-2-one). The modification provided us a quick and effective way of developing the new herbicides.

It was decided to keep the major functional carbonyl group of 3-acetyl-5-sec-butyl-4-hydroxy-3-pyrrolin-2-one and modify the hydrophobic 5-sec-butyl chain and the 3-acetyl group. A large number of derivatives were synthesized using phosphorous ylides and halogenated amino acids as precursors. Recently, a new synthetic route was developed, which no longer uses phosphor ylides and halogenated amino acids as starting materials. The new process starts from an amino acid and the 4 step reaction sequence is carried out in one pot without isolation and purification of any intermediates.

The synthetic pathway is as follows:

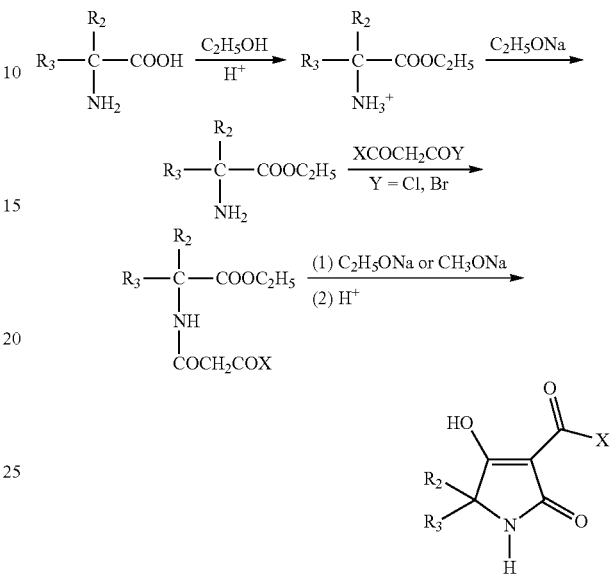

wherein
X=H; —$C_mH_{2m+1}$ substituted or unsubstituted; —$OC_mH_{2m+1}$ substituted or unsubstituted; —$C_mH_{2m-1}$ substituted or unsubstituted, —$OC_mH_{2m-1}$ substituted or unsubstituted; a substituted heterocyclic, an aryl, a phenylalkyl, a heterocycloalkyl-phenyl, a heterocycloalkyl, a heterocycloalkoxy, a phenoxy, or a phenoxyphenyl; the substituent groups being a halogen, a cyano, a nitro, an alkyoxyalkyl, an alkyoxycarbonyl, and/or an amido;

m represents from 1 to 7 carbon atoms; and $R_2$, and $R_3$ independently and at each occurrence represent H, —$CH_3$, —$C_2H_5$, —$CH_2CH_2CH_3$, —$CH(CH_3)_2$, —$(CH_2)_3CH_3$, —$C(CH_3)_3$, —$CH_2CH(CH_3)CH_3$, —$CH(CH_3)CH_2CH_3$, —$(CH_2)_4CH_3$, —$CH(CH_3)CH_2CH_2CH_3$, —$CH_2CH(CH_3)CH_2CH_3$, —$CH_2CH_2CH(CH_3)_2$, —$CH(CH_2CH_3)_2$, —$C(CH_2)_2C_2H_5$, —$(CH_2)_5CH_3$, —$CH(CH_3)(CH_2)_3CH_3$, —$CH_2CH(CH_3)(CH_2)_2CH_3$, —$CH_2CH_2CH(CH_3)CH_2CH_3$, —$(CH_2)_3CH(CH_3)_2$, —$CH(CH_2CH_3)CH_2CH_2CH_3$, —$CH_2CH(CH_2CH_3)_2$, —$C(CH_3)_2(CH_2)_2CH_3$, —$C(CH_3)CH_2CH_3)_2$, —$(CH_2)_6CH_3$, —$CH(CH_2CH_2CH_3)_2$, —$CH_2CH_2CH(CH_2CH_3)_2$, —$CH(CH_2CH_3)(CH_2)_3CH_3$, —$CH_2CH(CH_2CH_3)CH_2CH_2CH_3$, —$CH(CH_3)(CH_2)_4CH_3$, —$CH_2CH(CH_3)(CH_2)_3CH_3$, —$(CH_2)_2CH(CH_3)(CH_2)_2CH_3$, —$(CH_2)_3CH(CH_3)$ $CH_2CH_3$, —$(CH_2)_7CH_3$, —$CH_2CH(CH_2CH_2CH_3)_2$, —$CH(CH_2CH_2CH_3)(CH_2)_3CH_3$, —$CH(CH_3)(CH_2)_5CH_3$, —$CH_2CH(CH_3)(CH_2)_4CH_3$, —$(CH_2)_2CH(CH_3)(CH_2)_3$ $CH_3$, —$(CH_2)_3CH(CH_3)(CH_2)_2CH_3$, —$(CH_2)_4CH(CH_3)$ $CH_2CH_3$, —$CH(CH_2CH_3)(CH_2)_4CH_3$, —$(CH_2)_3CH$ $(CH_2CH_3)_2$, —$CH_2CH(CH_2CH_3)(CH_2)_3CH_3$, —$(CH_2)_2CH$ $(CH_2CH_3)(CH_2)_2CH_3$, —$CH=CH_2$, —$CH=CHCH_3$, —$CH_2CH=CH_2$, —$CH=CHCH_2CH_3$, —$CH_2CH_2CH=CH_2$, —$CH_2CH=CHCH_3$, —$CH=CH$— $CH=CH_2$, —CN, phenyl, —$CHClCH_3$, —$CHClCH_2CH_3$, —$CHClC_3H_7$, —$CHClC_4H_9$, —$CHClC_5H_{11}$, —$CHClC_6H_{13}$, —$CHClC_7H_{15}$, —$CHFCH_3$, —$CHFCH_2CH_3$, —$CHFC_3H_7$, —$CHFC_4H_9$, —$CHFC_5H_{11}$, —CHFC$_6$H$_{13}$, —CHFC$_7$H$_{15}$, —CHCNCH$_3$, —CHCNCH$_2$CH$_3$, —CHCNC$_3$H$_7$, —CHCNC$_4$H$_9$, —CHCNC$_5$H$_{11}$, —CHCNC$_6$H$_{13}$, —CHCNC$_7$H$_{15}$, —CH(C$_6$H$_5$)CH$_3$, —CH(C$_6$H$_5$)CH$_2$CH$_3$, —CH(C$_6$H$_5$)C$_3$H$_7$, —CH(C$_6$H$_5$)C$_4$H$_9$, —CH(C$_6$H$_5$)C$_5$H$_{11}$, —CH(C$_6$H$_5$)C$_6$H$_{13}$, —CH(C$_6$H$_5$)C$_7$H$_{15}$, —CHClCH=CH$_2$, or —CHClCH$_2$CH=CH$_2$.

When X is a methyl group, the following synthetic method can also be used:

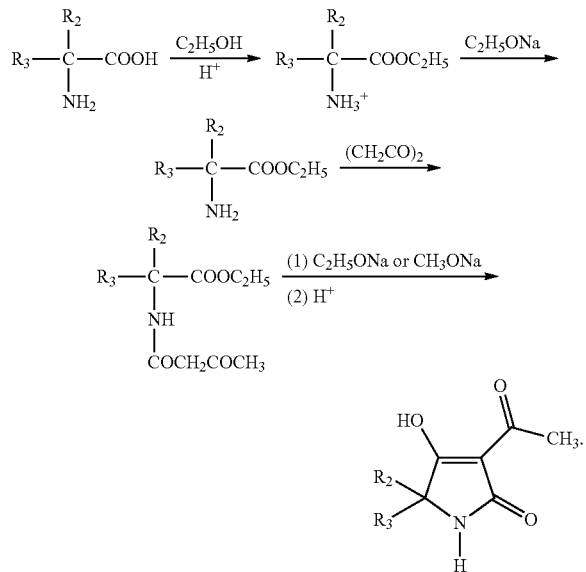

3-acetyl-5-sec-butyl-4-hydroxy-3-pyrrolin-2-one analogs were dissolved in a small amount of methanol and diluted with water to a concentration of 5-100 μg/g. A pathogenic test was conducted by placing the toxic liquid on the slightly wounded leaf of Crofton weed with a needle. The test has shown that the pathogenic capability of 3-acetyl-5-sec-butyl-4-hydroxy-3-pyrrolin-2-one analogs with respect to Crofton weed increases with the increase of concentration. The spot diameter caused on the leaf of Crofton weed after 24 hours was 2 mm at 50 μg/g.

The mechanism of action of 3-acetyl-5-sec-butyl-4-hydroxy-3-pyrrolin-2-one analogs on weeds is to affect plant photosynthesis. Specifically, it significantly reduces the photosynthetic oxygen evolution rate and the apparent quantum efficiency. The main action site of the compounds is the thylakoid membrane, inhibiting the electron transfer reaction of two photosystems, especially photosystem II, but no effect has been observed on the structure and synthesis of the membrane protein. In addition, the active oxygen content significantly has been increased 3 hours after the leaf was treated with 3-acetyl-5-sec-butyl-4-hydroxy-3-pyrrolin-2-one analogs. This may be the cause of cell death and appearance of the brown spots on the leaf. Moreover, it may also block the synthesis of protein in the ribosome.

The main advantages and positive effects of the invention are summarized below: modification of 3-acetyl-5-sec-butyl-4-hydroxy-3-pyrrolin-2-one was carried out, based on (1): its inhibitory activity to photosystem II and its binding mode to D1 protein; and (2): its inhibitory activity and its action sites, combined with chemical synthetic route of 3-acetyl-4-hydroxy-5-sec-butylpyrroline-2-ketone. Focus was placed on the carbonyl oxygen (a few hydroxyl oxygens), which played essential role in the protein binding. The structure of D1 protein from algae was carefully analyzed and of various factors including hydrophobicity, electronegativity and stereo hindrance were considered when designing and selecting the target molecules. It is obvious that such rational design has advantage over the traditional chemical herbicide screening.

A series of herbicidal molecules was prepared through the modification of 3-acetyl-5-sec-butyl-4-hydroxy-3-pyrrolin-2-one, a metabolic phytotoxin of *Alternaria alternata*. These compounds kill weeds quickly; the weeds treated with the herbicidal agents clearly show symptoms after 24 hours, and the weeds can be killed in about 3 to 5 days.

The method of biocontrolling weeds using the analogues of tenuazonic acid and their salts effectively controls and eradicates the main gramineous weeds in the farmland, such as common crabgrass, barnyardgrass, goosegrass, green foxtail, equal alopecurus, Japanese alopecurus, Beckmannia syzigachne Fern, wild oat, annual bluegrass, keng stiffgrass, common polypogon, and rabbitfoot polypogon; broad leaf weeds, such as Crofton weed, Copperleaf, Yerbadetajo, Redroot pigweed, Tender catchweed bedstraw, Narrowleaf vetch, Sheathed monochoria, Indian rotala, Water ammannia, Purslane, Flixweed tansymustard, Shepherdspurse, Common dayflower, Wild cress, Wormseed mustard, Pennsylvania bittercress, Geminate speedwell, Mouse-ear chickweed; and sedges, such as Needle spikesedge, Difformed galingale, Rice galingale, and *Dichotomous dimbristylis*.

The compounds of the invention have high activity at concentration as low as from 5 to 50 μg/g. At a concentration of 10 to 800 μg/g (close to 45-360 g/hectare), the compounds can kill a variety of broad-leaf weeds, grassy weeds, and sedge weeds. They are highly potential herbicides.

The analogues disclosed herein have comparable herbicidal activity to the original tenuazonic acid. These molecules are easy to make, thus reducing the manufacturing cost. Because these compounds were obtained through modification of the metabolite of a fungus, a natural product, these analogs have some desirable characteristics of biobased herbicides: low pollution, few byproducts, high rate of decomposition, and high environmental safety.

The new synthetic process can be carried out in one pot without isolation and purification of the intermediates. This process can reduce the manufacturing cost.

DETAILED DESCRIPTION OF THE EMBODIMENTS

The following examples illustrate the products of this invention and the methods for preparing them. However, the examples are not intended in any way to otherwise limit the scope of the invention. The number of compounds that were synthesized and evaluated is far exceeding the number of examples.

Example 1

List of Compounds Having Formula (I) and (II) (Table 1) and Herbicidal Activities Thereof (Table 2)

Synthesis of compound 1: A 100 mL three-neck flask was charged with anhydrous alcohol (30 mL), hydrogen chloride (0.055 mol, 2 g) and Isoleucine (0.05 mol, 6.56 g). The mixture was heated to reflux and stirred for 3 h and then left overnight. Ethanol was removed by distillation and the residue was mixed with sodium ethoxide (0.05 mol, 2.6 g, freshly prepared) solution in ethanol. The mixture was stirred for 0.5 h. Cyclobutane-1,3-dione (0.055 mol, 4.62 g) was added over 1 h, with the temperature kept below 10° C., and the reaction was stirred for 2 h. Benzene (20 ml) and sodium ethoxide (0.0575 mol, 3 g, freshly prepared) solution in ethanol were added, and the mixture was stirred at reflux for 3 h and allowed to stand at room temperature overnight. The reaction mixture was poured into 30 mL of water and acidified with 10% sulfuric acid (0.055 mol, 55 g), then extracted with ethyl acetate and dried over sodium sulfate. Ethyl acetate was removed under vacuum and the residue was mixed with concentrated sulfuric acid and toluene. The mixture was refluxed in toluene for 2 h. Compound 1 was obtained as a brown solid after column chromatography in a 55.6% yield.

Synthesis of compound 9: A 100 mL three-neck flask was charged with anhydrous alcohol (30 mL), hydrogen chloride (0.055 mol, 2 g) and Isoleucine (0.05 mol, 6.56 g). The mixture was heated to reflux and stirred for 3 h and then left overnight. Ethanol was removed by distillation and the residue was mixed with sodium ethoxide (0.05 mol, 2.6 g, freshly prepared) solution in ethanol and stirred for 0.5 h. 2-Propionamidoacetyl chloride (0.055 mol, 8.22 g) was added over 1 h and the reaction was stirred for 2 h. Benzene (20 ml) and sodium ethoxide (0.0575 mol, 3 g, freshly prepared) solutions were added, and the mixture was stirred at reflux for 3 h and allowed to stand at room temperature overnight. The reaction mixture was poured into 30 mL of water and acidified with 10% sulfuric acid (0.055 mol, 55 g), then extracted with ethyl acetate and dried over sodium sulfate. Removal of ethyl acetate under vacuum gave crude product which was purified with column chromatography, providing compound 9 as a pale brown oil in a 47.1% yield.

Example 2

Herbicidal Activity Evaluation of Compounds 10-57 with Formula (III), (IV), and (V) (Table 3)

Synthesis of compound 24: A 100 mL three-neck flask was charged with anhydrous alcohol (30 mL), hydrogen chloride (0.055 mol, 2 g) and 2-amino-2-methylbutanoic acid (0.05 mol, 5.85 g). The mixture was heated to reflux and stirred for 3 h and then left for overnight. Ethanol was removed by distillation and the residue was mixed with sodium ethoxide (0.05 mol, 2.6 g, freshly prepared) solution in ethanol and stirred for 0.5 h. Cyclobutane-1,3-dione (0.055 mol, 4.62 g) was added over 1 h maintaining the temperature of the reaction mixture below 10° C., and the reaction was stirred for 2 h. Benzene (20 ml) and sodium ethoxide (0.0575 mol, 3 g, freshly prepared) solution in ethanol were added, and the mixture was stirred at reflux and then allowed to stand for 3 h at room temperature overnight. The reaction mixture was mixed with 30 mL of water and acidified with 10% sulfuric acid (0.055 mol, 55 g), then extracted with ethyl acetate and dried over sodium sulfate. Removal of ethyl acetate under vacuum gave crude product, which was purified with column chromatography, providing compound 24 as a pale brown oil in a 52.9% yield.

Synthesis of Compound 53: A 100 mL of three-neck flask was charged with anhydrous alcohol (30 mL), hydrogen chloride (0.055 mol, 2 g) and 2-amino-3-cyanohexanoic acid (0.05 mol, 7.81 g). The mixture was heated to reflux and stirred for 3 h and then left overnight. Ethanol was removed by distillation and the residue was mixed with sodium ethoxide (0.05 mol, 2.6 g, freshly prepared) solution in ethanol, and stirred for 0.5 h. Cyclobutane-1,3-dione (0.055 mol, 4.62 g) was added over 1 h and maintaining the temperature of the reaction mixture below 10° C., and the reaction was stirred for 2 h. Benzene (20 mL) and sodium ethoxide (0.0575 mol, 3 g, freshly prepared) solution in ethanol were added, and the mixture was stirred at reflux for 3 h and then to allowed to stand at room temperature overnight. The reaction mixture was mixed with 30 mL of water and acidified with 10% sulfuric acid (0.055 mol, 55 g), extracted with ethyl acetate and dried over sodium sulfate. Removal of ethyl acetate under vacuum gave crude product, which was purified with column chromatography, providing compound 53 as a brown oil in 45% yield.

TABLE 1

Physical properties of 3-acetyl-4-hydroxy-5-sec-butylpyrroline-2-ketone analogs with formula (I) and (II)

| Compound | Type | $R_1$ | $R_2$ | $R_3$ | Appearance |
|---|---|---|---|---|---|
| 1 | II | H | Sec-$C_4H_9$ | H | Brown solid |
| 2 | II | H | $C_3H_7$CHCl | H | Brown solid |
| 3 | I | H | Sec-$C_4H_9$ | H | Light brown viscous liquid |
| 4 | I | $CH_3CH_2$ | Sec-$C_4H_9$ | H | Light brown viscous liquid |
| 5 | I | $C_2H_5O$ | Sec-$C_4H_9$ | H | Light brown viscous liquid |
| 6 | I | $C_6H_5CH_2CH_2$ | Sec-$C_4H_9$ | H | Light brown viscous liquid |
| 7 | I | $NH_2COCH_3CH_2$ | Sec-$C_4H_9$ | H | Light brown viscous liquid |
| 8 | I | $Cl(CH_2)_3NH$ | Sec-$C_4H_9$ | H | Light brown viscous liquid |
| 9 | I | $C_2H_5CONH$ | Sec-$C_4H_9$ | H | Light brown viscous liquid |

TABLE 2

Comparison of the toxicity of 3-acetyl-4-hydroxy-5-sec-butylpyrroline-2-ketone analogs with formula (I) and (II)

| Treatment | Time of disease spot to occur (h) | Avg. diameter of the spot after 24 h (mm) |
|---|---|---|
| Water control | / | 0.23 ± 0.02 |
| Methanol control | / | 0.27 ± 0.14 |
| 1 | 22.3 ± 0.77 | 1.97 ± 0.04 |
| 2 | 22.0 ± 2.30 | 2.96 ± 0.01 |
| 3 | 20.9 ± 1.01 | 2.31 ± 0.09 |
| 4 | 18.5 ± 1.55 | 2.97 ± 0.01 |
| 5 | 20.7 ± 0.75 | 2.35 ± 0.14 |
| 6 | 21.2 ± 3.85 | 2.12 ± 0.08 |
| 7 | 14.9 ± 2.65 | 4.45 ± 0.22 |
| 8 | 20.0 ± 1.51 | 2.53 ± 0.18 |
| 9 | 21.9 ± 2.00 | 2.80 ± 0.33 |

TABLE 3

Physical properties of 3-Acetyl-4-hydroxy-5-sec-butylpyrroline-2-ketone analogues with formula of (III), (IV), and (V)

| Compound | Type | X | $R_2$ | $R_3$ | Appearance |
|---|---|---|---|---|---|
| 10 | III | $CH_3$ | H | H | Light yellow solid |
| 11 | III | $CH_3$ | $CH_3$ | H | Pale needle crystal |
| 12 | III | $CH_3$ | $CH_3CH_2$ | H | Light brown solid |
| 13 | III | $CH_3$ | $CH_3CH_2CH_2$ | H | Light brown viscous liquid |
| 14 | III | $CH_3$ | n-$C_4H_9$ | H | Light brown viscous liquid |
| 15 | III | $CH_3$ | n-$C_5H_{11}$ | H | Light brown viscous liquid |
| 16 | III | $CH_3$ | n-$C_6H_{13}$ | H | Light brown oil |
| 17 | III | $CH_3$ | n-$C_7H_{15}$ | H | Light brown oil |
| 18 | III | $CH_3$ | n-$C_8H_{17}$ | H | Light brown oil |
| 19 | III | $CH_3$ | $C_6H_5CH_2$ | H | Light yellow solid |
| 20 | III | $CH_3$ | (1-$C_6H_5$)$C_4H_8$ | H | Light yellow solid |
| 21 | III | $CH_3$ | $H_3C$—CH:CH | H | Brown viscous liquid |
| 22 | III | $CH_3$ | $CH_3$ | $CH_3$ | Light yellow solid |
| 23 | III | $CH_3$ | $CH_3CH_2$ | $CH_3CH_2$ | Light brown viscous liquid |
| 24 | III | $CH_3$ | $CH_3CH_2$ | $CH_3$ | Light brown viscous liquid |
| 25 | III | $CH_3$ | $CH_3CH_2CH_2$ | $CH_3CH_2CH_2$ | Light brown viscous liquid |
| 26 | III | $CH_3$ | $CH_3CH_2CH_2$ | $CH_3$ | Light brown viscous liquid |
| 27 | III | $CH_3$ | $CH_3CH_2CH_2$ | $CH_3CH_2$ | Light brown viscous liquid |
| 28 | III | $CH_3$ | n-$C_4H_9$ | n-$C_4H_9$ | Light brown viscous liquid |
| 29 | III | $CH_3$ | n-$C_4H_9$ | $CH_3$ | Light brown viscous liquid |
| 30 | III | $CH_3$ | n-$C_4H_9$ | $CH_3CH_2$ | Light brown viscous liquid |
| 31 | III | $CH_3$ | sec-$C_5H_{11}$ | H | Light yellow liquid |
| 32 | III | $CH_3$ | tert-$C_5H_{11}$ | H | Light yellow liquid |
| 33 | III | $CH_3$ | iso-$C_5H_{11}$ | H | Light yellow liquid |
| 34 | III | $CH_3$ | $OOCCH_2$ | H | Light yellow solid |
| 35 | III | $CH_3$ | $OOCCH_2CH_2$ | H | Light yellow solid |
| 36 | III | $CH_3$ | $(NH_2)OCCH_2$ | H | Light yellow solid |
| 37 | III | $CH_3$ | $(NH_2)OCCH_2CH_2$ | H | Light yellow solid |
| 38 | III | $CH_3$ | $C_3H_7$CHCN | H | Light brown viscous liquid |
| 39 | III | $CH_3$ | iso-$C_3H_7$ | H | Light brown solid |
| 40 | III | $CH_3$ | $C_3H_7$CHCl | H | Light brown viscous liquid |
| 41 | III | $CH_3$ | $CH_3SCH_2CH_2$ | H | Light brown solid |
| 42 | III | $C_2H_5$ | sec-$C_4H_9$ | H | Light brown viscous liquid |
| 43 | III | $ClC_2H_4$ | sec-$C_4H_9$ | H | Light brown viscous liquid |
| 44 | III | $FC_2H_4$ | sec-$C_4H_9$ | H | Light brown viscous liquid |
| 45 | III | $C_2H_5OC_2H_5$ | sec-$C_4H_9$ | H | Light brown viscous liquid |
| 46 | III | $PhCH_2CH_2O$ | sec-$C_4H_9$ | H | Light brown viscous liquid |
| 47 | III | $PhOCH_2CH_2$ | sec-$C_4H_9$ | H | Light brown viscous liquid |
| 48 | III | (m-diCl)$PhCH_2CH_2$ | sec-$C_4H_9$ | H | Light brown viscous liquid |
| 49 | III | $PhCH_2NH$ | sec-$C_4H_9$ | H | Light brown viscous liquid |
| 50 | III | THF—$CH_2CH_2$ | sec-$C_4H_9$ | H | Light brown viscous liquid |
| 51 | III | $PhCH_2$ | sec-$C_4H_9$ | H | Light brown viscous liquid |
| 52 | III | p-$NO_2PhCH_2$ | sec-$C_4H_9$ | H | Light brown viscous liquid |
| 53 | IV | $CH_3$ | $C_3H_7$CHCN | H | Brown viscous liquid |
| 54 | IV | $CH_3$ | $C_5H_{11}$CHCN | H | Brown oil liquid |
| 55 | IV | $CH_3$ | $C_7H_{13}$CHCN | H | Brown oil liquid |
| 56 | IV | $CH_3$ | $C_7H_{13}$CHF | H | Brown oil liquid |
| 57 | V | $CH_3$ | $CH_3$ | H | Yellow needle crystal |

The study results showed different herbicidal activities of the above compounds. The compounds also affect the Hill reaction rate and fluorescence of thechlorophyll.

Example 3

3-acetyl-5-sec-butyl-4-hydroxy-3-pyrrolin-2-one analogue (Table 3, compounds 10-57) was dissolved in small amount of methanol. The solution was then diluted with distilled water to a concentration of 50 μg/mL. Methanol solution with same concentration and pure distilled water were used as control of the experiment. A pathogenic test was conducted by placing the toxic liquid on the slightly wounded leaf of Crofton weed with a needle. The experiment was carried out at 25° C. under the natural light and each test was repeated 6 times. It was measure the diameter of the spot after 24 h. The experimental results are listed in Table 4. The data indicated that most of the 3-acetyl-5-sec-butyl-4-hydroxy-3-pyrrolin-2-one analogs have high herbicidal activity. The size of the side chain also has an effect on their activity.

TABLE 4

Comparison of the toxicity of 3-acetyl-4-hydroxy-5-sec-butylpyrroline-2-ketone analogs with formula (III), (IV), and (V)

| Treatment | Time of Disease spot (h) | Average diameter of spot after 24 h (mm) |
|---|---|---|
| Water control | / | 0.23 ± 0.02 |
| Methanol control | / | 0.27 ± 0.14 |
| 10 | 29 ± 6.30 | 1.11 ± 0.16 |
| 11 | 21.5 ± 0 | 1.80 ± 0.41 |
| 12 | 15.2 ± 0.35 | 2.77 ± 0.23 |
| 13 | 16.70 ± 0.21 | 5.21 ± 0.44 |
| 14 | 13.8 ± 0.54 | 6.37 ± 0.04 |
| 15 | 9.5 ± 1.26 | 9.61 ± 1.20 |
| 16 | 13.80 ± 0.54 | 7.61 ± 0.11 |

TABLE 4-continued

Comparison of the toxicity of 3-acetyl-4-hydroxy-
5-sec-butylpyrroline-2-ketone analogs with formula (III), (IV), and (V)

| Treatment | Time of Disease spot (h) | Average diameter of spot after 24 h (mm) |
|---|---|---|
| 17 | 9.5 ± 2.36 | 7.94 ± 1.30 |
| 18 | 12.00 ± 0.48 | 8.27 ± 0.61 |
| 19 | 24 ± 4.00 | 1.24 ± 0.10 |
| 20 | 21.1 ± 3.56 | 1.57 ± 0.04 |
| 21 | 16.5 ± 1.30 | 2.89 ± 0.14 |
| 22 | 20.0 ± 1.63 | 1.76 ± 0.24 |
| 23 | 18.3 ± 2.17 | 2.23 ± 0.12 |
| 24 | 16.21 ± 3.55 | 2.43 ± 0.07 |
| 25 | 15.22 ± 2.00 | 2.44 ± 0.10 |
| 26 | 13.61 ± 1.35 | 3.31 ± 0.07 |
| 27 | 14.2 ± 4.15 | 3.18 ± 0.93 |
| 28 | 16.9 ± 2.25 | 2.40 ± 0.11 |
| 29 | 12.1 ± 3.75 | 5.77 ± 1.15 |
| 30 | 13.3 ± 2.00 | 4.53 ± 1.03 |
| 31 | 10.8 ± 2.00 | 5.93 ± 1.35 |
| 32 | 12.5 ± 3.75 | 4.82 ± 1.44 |
| 33 | 13.5 ± 0.75 | 4.17 ± 1.15 |
| 34 | 24.0 ± 0.02 | 1 ± 0.86 |
| 35 | 26.4 ± 0.12 | 1.27 ± 0.02 |
| 36 | 21.9 ± 0.23 | 1.54 ± 0.07 |
| 37 | 24 ± 0.08 | 1.64 ± 0.25 |
| 38 | 13.6 ± 0.50 | 9.82 ± 0.02 |
| 39 | 16.5 ± 2.15 | 4.89 ± 0.37 |
| 40 | 11.93 ± 0.66 | 8.10 ± 0.90 |
| 41 | 20.8 ± 3.00 | 2.45 ± 0.24 |
| 42 | 19.4 ± 2.50 | 2.24 ± 0.45 |
| 43 | 20.1 ± 1.15 | 2.30 ± 0.28 |
| 44 | 12.0 ± 1.33 | 4.07 ± 0.51 |
| 45 | 20.3 ± 0.57 | 2.73 ± 0.73 |
| 46 | 22.1 ± 1.35 | 2.31 ± 0.44 |
| 47 | 21.2 ± 1.88 | 2.12 ± 0.09 |
| 48 | 13.5 ± 2.77 | 4.33 ± 0.54 |
| 49 | 23.2 ± 2.86 | 2.47 ± 0.08 |
| 50 | 22.6 ± 0.69 | 2.66 ± 0.46 |
| 51 | 15.1 ± 1.82 | 3.28 ± 1.12 |
| 52 | 15.3 ± 1.72 | 3.83 ± 1.03 |
| 53 | 12.90 ± 0.27 | 7.334 ± 0.845 |
| 54 | 11.30 ± 0.73 | 8.211 ± 0.101 |
| 55 | 9.81 ± 0.33 | 8.931 ± 0.086 |
| 56 | 14.00 ± 1.09 | 6.927 ± 0.317 |
| 57 | 20.4 ± 0 | 1.98 ± 0.51 |

Example 4

Compounds 1, 2, 3, and 40 were separately dissolved in a small amount of methanol. The solutions were then diluted with distilled water to a concentration of 50 µg/mL. A mixture of methanol and water in the same ratio as the sample solution was also prepared and used as control in the experiment. The solutions were sprayed on leaves and stems of three-leaf-stage Crofton weed seedlings. All the plants were grown in pot in a greenhouse. The leaves were properly wet by the solutions for consistency and the treatment was repeated 3 times. The plant damage assessment was conducted two days later and the results were listed in Table 5. The measurement of the plant damage was calculated by the formula: Damage Index=Σ(damage level×number of plants)×100/4/number of plants in each treatment. The calculated results are listed in Table 6.

TABLE 5

Standard of evaluation of weed damage

| Damage Level | Description |
|---|---|
| 4 | Plant completely dead |
| 3 | Two thirds of the plant stems and leaves dried out |
| 2 | Half of the plant stems and leaves dried out |
| 1 | One third of the plant stems and leaves dried out |
| 0 | No damage at all |

TABLE 6

Weed damage assessment results

| Treatment | Damage Level |
|---|---|
| H₂O control | 0 |
| Methanol control | 0 |
| 1 | 2 |
| 2 | 2 |
| 3 | 1 |
| 40 | 4 |

The data in the Table 6 suggests that the analogs of 3-acetyl-5-sec-butyl-4-hydroxy-3-pyrrolin-2-one have good herbicidal activity against Crofton weed. Substitution of chlorine on the side chain increases their activity.

Example 5

Compounds 10-57 were dissolved in small amount of methanol. The solutions were then diluted with distilled water to a concentration of 50 µg/mL. A mixture of methanol and water in the same ratio as the sample solution was also prepared and used as control in the experiment. The healthy leaves of Crofton weed were washed in water for 30 minutes and then rinsed with distilled water. The clean and tissue dried leaves were placed in petri dish with the back-side of the leaves facing up. Wet filter paper was also placed in the in petri dish for moisture control. Water, methanol and chemical solutions of the analogues were applied to the back-side of each leaf. Test sample was then placed in vacuum chamber at 25° C. for 15 min followed by exposure to the strong light (400 µM m$^{-2}$ s$^{-1}$) for 12 hours. The leaf sample went through a series of test, and the Hill reaction rate, the electron transfer activity and fluorescence of chlorophyll were measured. Four leaves were used for each treatment and each test was repeated three times.

The experiment results indicate that compound 10 to 57 can slow the Hill reaction and inhibit the electron transfer of photosystem II, but has no effect in photosystem I. As the experimental data in Table 7 indicated that compounds having chlorinated side-chain have more inhibitory effect on the activity of Hill reaction and electron transfer in photosystem II than the compounds whose side chain are not substituted by halogen.

TABLE 7

Effects to the photosynthesis of Crofton weed

| Treatment | Activity of Hill Reaction (uMO₂/mgChlh) | PSII Activity of oxygen evolution of (uMO₂/mgChlh) | $F_v/F_m$ | The $t_{1/2}$ of fluorescence rise (ms) |
|---|---|---|---|---|
| H₂O control | 130.11 | 65.34 | 0.83 | 1339 |
| Methanol control | 124.38 | 60.89 | 0.81 | 1382 |
| 1 | 98.76 | 50.89 | 0.82 | 1184 |
| 2 | 69.41 | 37.02 | 0.84 | 1055 |

TABLE 7-continued

Effects to the photosynthesis of Crofton weed

| Treatment | Activity of Hill Reaction (uMO$_2$/mgChlh) | PSII Activity of oxygen evolution of (uMO$_2$/mgChlh) | $F_v/F_m$ | The $t_{1/2}$ of fluorescence rise (ms) |
|---|---|---|---|---|
| 3 | 62.21 | 32.14 | 0.83 | 1172 |
| 4 | 51.13 | 28.01 | 0.83 | 791 |
| 5 | 52.31 | 24.10 | 0.82 | 826 |
| 6 | 50.04 | 27.11 | 0.81 | 773 |
| 7 | 52.41 | 29.17 | 0.82 | 809 |
| 8 | 49.05 | 24.65 | 0.79 | 725 |
| 9 | 50.12 | 23.33 | 0.83 | 733 |
| 10 | 84.32 | 47.55 | 0.79 | 1176 |
| 11 | 80.00 | 46.41 | 0.82 | 1181 |
| 12 | 70.32 | 34.54 | 0.83 | 925 |
| 13 | 78.19 | 41.35 | 0.85 | 1000 |
| 14 | 67.37 | 34.01 | 0.79 | 910 |
| 15 | 62.77 | 31.26 | 0.78 | 946 |
| 16 | 61.43 | 30.00 | 0.83 | 880 |
| 17 | 57.13 | 27.04 | 0.82 | 917 |
| 18 | 67.27 | 39.98 | 0.80 | 913 |
| 19 | 63.43 | 40.07 | 0.79 | 962 |
| 20 | 57.23 | 43.40 | 0.82 | 876 |
| 21 | 62.34 | 42.25 | 0.77 | 879 |
| 22 | 56.16 | 38.05 | 0.82 | 828 |
| 23 | 63.28 | 38.24 | 0.79 | 855 |
| 24 | 71.37 | 43.01 | 0.83 | 921 |
| 25 | 97.55 | 57.12 | 0.82 | 1197 |
| 26 | 89.15 | 58.01 | 0.82 | 1211 |
| 27 | 91.45 | 53.24 | 0.81 | 1232 |
| 28 | 75.03 | 31.76 | 0.82 | 1124 |
| 30 | 47.33 | 22.78 | 0.79 | 747 |
| 32 | 63.42 | 32.13 | 0.82 | 905 |
| 33 | 51.94 | 26.54 | 0.79 | 791 |
| 34 | 65.73 | 35.11 | 0.81 | 922 |
| 38 | 64.69 | 40.41 | 0.81 | 871 |
| 39 | 62.72 | 33.79 | 0.80 | 884 |
| 40 | 46.20 | 24.00 | 0.82 | 720 |
| 41 | 59.07 | 41.32 | 0.83 | 901 |
| 43 | 63.35 | 47.80 | 0.83 | 880 |
| 44 | 59.15 | 40.75 | 0.79 | 839 |
| 45 | 41.00 | 27.04 | 0.79 | 713 |
| 46 | 58.78 | 43.67 | 0.82 | 899 |
| 47 | 67.99 | 49.01 | 0.82 | 844 |
| 51 | 52.23 | 32.15 | 0.81 | 798 |
| 52 | 53.13 | 36.86 | 0.82 | 814 |
| 53 | 42.72 | 32.12 | 0.79 | 739 |
| 54 | 43.65 | 31.98 | 0.81 | 741 |
| 55 | 42.72 | 28.63 | 0.79 | 727 |
| 56 | 42.72 | 29.02 | 0.79 | 719 |
| 57 | 63.42 | 35.13 | 0.82 | 955 |

Example 6

Fourteen salts of 3-acetyl-5-sec-butyl-4-hydroxy-3-pyrrolin-2-one analogs were dissolved in small amount of methanol and diluted with distilled water to a concentration of 50 μg/mL. Methanol/water mixture was also prepared and used as control. Needle puncture method was used for the test on the small pieces of Crofton weed. Each treatment was repeated six times or more. The test samples were kept under natural light at 25° C. for 24 hours. The diameters of damaged spot of the plant leaves were measured by vernier caliper. These fourteen compounds are:

(a) Sodium salt of 3-acetyl-4-hydroxy-1H-pyrrol-2(5H)-one

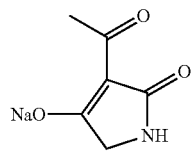

(b) Sodium salt of 3-acetyl-4-hydroxy-5-methyl-1H-pyrrol-2(5H)-one

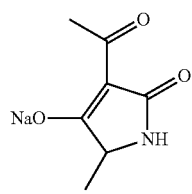

(c) Sodium salt of 3-acetyl-5-ethyl-4-hydroxy-1H-pyrrol-2(5H)-one

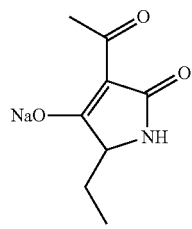

(d) Sodium salt of 3-acetyl-4-hydroxy-5-propyl-1H-pyrrol-2(5H)-one

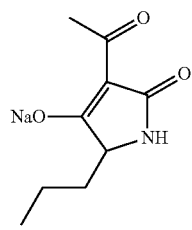

(e) Sodium salt of 3-acetyl-4-hydroxy-5-(prop-1-enyl)-1H-pyrrol-2(5H)-one

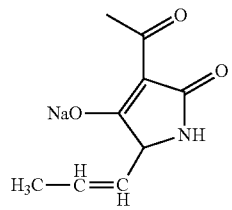

(f) Potassium salt of 3-acetyl-5-ethyl-4-hydroxy-1H-pyrrol-2(5H)-one

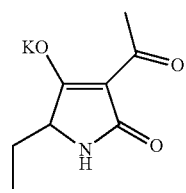

(g) Calcium salt of 3-acetyl-5-ethyl-4-hydroxy-1H-pyrrol-2(5H)-one

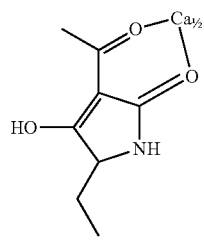

(h) Magnesium (II) salt of 3-acetyl-5-ethyl-4-hydroxy-1H-pyrrol-2(5H)-one

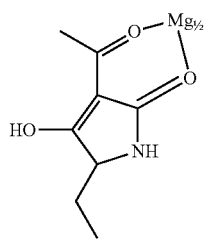

(i) Manganese salt of 3-acetyl-5-ethyl-4-hydroxy-1H-pyrrol-2(5H)-one

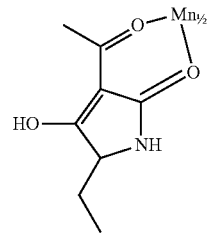

(j) Zinc salt of 3-acetyl-5-ethyl-4-hydroxy-1H-pyrrol-2(5H)-one

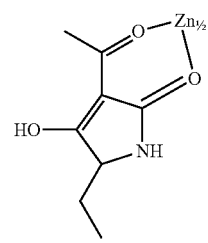

(k) Iron salt of 3-acetyl-5-ethyl-4-hydroxy-1H-pyrrol-2(5H)-one

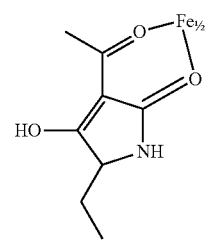

(l) Copper salt of 3-acetyl-5-ethyl-4-hydroxy-1H-pyrrol-2(5H)-one

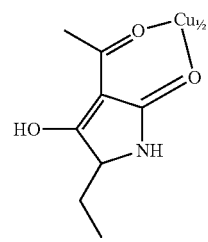

(m) Sodium salt of 3-acetyl-4-hydroxy-5-(Pentan-2-yl)-1H-pyrrol-2(5H)-one

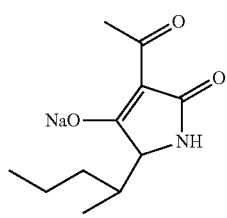

(n) Zinc salt of 3-acetyl-4-hydroxy-5,5-dimethyl-1H-pyrrol-2(5H)-one

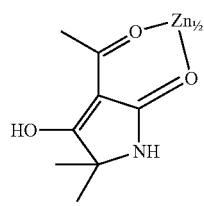

(o) Ammonium salt of 3-acetyl-5-ethyl-4-hydroxy-1H-pyrrol-2(5H)-one

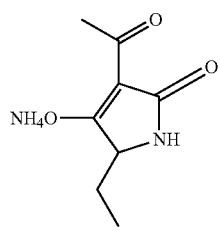

TABLE 8

Herbicidal activity of 14 salts to Crofton weed

| Treatment | Time (h) | Average diameter of the damage spot after 24 h (mm) |
|---|---|---|
| H₂O control | / | 0.227 ± 0.002 |
| Methanol control | / | 0.273 ± 0.014 |
| a | 26 ± 7.30 | 1.34 ± 0.08 |

TABLE 8-continued

Herbicidal activity of 14 salts to Crofton weed

| Treatment | Time (h) | Average diameter of the damage spot after 24 h (mm) |
|---|---|---|
| b | 19.5 ± 0.5 | 2.21 ± 0.18 |
| c | 14.5 ± 1.8 | 3.11 ± 0.54 |
| d | 10.2 ± 2.50 | 5.07 ± 0.11 |
| e | 16.8 ± 1.85 | 2.42 ± 0.05 |
| f | 14.2 ± 2.00 | 3.72 ± 0.28 |
| g | 18.7 ± 3.00 | 2.29 ± 0.19 |
| h | 17.5 ± 1.50 | 2.88 ± 0.10 |
| i | 14.3 ± 3.15 | 3.24 ± 0.33 |
| j | 15.1 ± 4.00 | 2.91 ± 0.02 |
| k | 17.2 ± 0.95 | 1.72 ± 0.15 |
| l | 21.6 ± 3.05 | 1.22 ± 0.25 |
| m | 8.5 ± 2.00 | 8.27 ± 1.72 |
| n | 18.2 ± 2.50 | 2.63 ± 0.06 |
| o | 10.3 ± 1.50 | 4.97 ± 1.01 |

Compared with the no-salt form (data are listed in Table 2 and Table 4), the salt form of these compounds is much more herbicidal. In addition, the ammonium salt, the sodium salt, the potassium salt, the magnesium salt and the zinc salt have higher activity than the calcium, magnesium and copper salts.

Example 7

Compounds 7, 14, 15, 16, 40, 45, 48 and 53 were dissolved individually in small amount of methanol, and diluted with distilled water to concentration of 50 μg/mL. Methanol water solution and pure water were used as control. A piece of 5 mm leaf was taken from the second leaf of weed sample and was treated with the solution three times. 5 pieces of the leaf were prepared for each treatment. The damage data were collected 4 days later. The measurement of damage level is described in the Table 9.

TABLE 9

Standard of evaluation of weed damage

| Damage level | Description |
|---|---|
| 4 | The leaf completely dead |
| 3 | Two third of the leaf withered |
| 2 | One half of the leaf withered |
| 1 | Only edge of the leaf withered |
| 0 | Not damage at all |

The measurement of the plant damage was calculated by the formula: Damage Index=Σ(damage level×number of plants)×100/4/number of plants in each treatment. The calculated results are listed in Table 10.

TABLE 10

Weed damage assessment results

| Family | Plant species | H₂O | Methanol | 7 | 14 | 15 | 16 | 40 | 44 | 48 | 53 |
|---|---|---|---|---|---|---|---|---|---|---|---|
| Gramineae | Goose grass | 0 | 0 | 4 | 3 | 3 | 3 | 4 | 3 | 3 | 4 |
| | Wild oats | 0 | 0 | 4 | 3 | 3 | 3 | 3 | 3 | 3 | 3 |
| | Equal *alopecurus* | 0 | 0 | 4 | 3 | 3 | 3 | 3 | 3 | 4 | 4 |
| | Japanese *alopecurus* | 0 | 0 | 4 | 3 | 3 | 3 | 3 | 4 | 4 | 3 |
| | Keng stiffgrass | 0 | 0 | 4 | 3 | 3 | 3 | 3 | 3 | 4 | 4 |
| | Common polypogon | 0 | 0 | 3 | 3 | 3 | 3 | 3 | 4 | 4 | 4 |
| | Green foxtail (*Setaria viridis*) | 0 | 0 | 4 | 3 | 4 | 3 | 3 | 4 | 4 | 3 |
| | Crabgrass (*Digitaria sanguinalis*) | 0 | 0 | 4 | 4 | 4 | 4 | 4 | 4 | 4 | 4 |

TABLE 10-continued

Weed damage assessment results

| Family | Plant species | H₂O | Methanol | 7 | 14 | 15 | 16 | 40 | 44 | 48 | 53 |
|---|---|---|---|---|---|---|---|---|---|---|---|
| | *Leptochloa chinensis* | 0 | 0 | 4 | 4 | 4 | 4 | 4 | 4 | 4 | 4 |
| | Barbyardgrass *Echinochloa crusgalli* | 0 | 0 | 4 | 4 | 4 | 4 | 4 | 4 | 4 | 4 |
| | Big Bristlegass | 0 | 0 | 3 | 2 | 2 | 3 | 3 | 2 | 3 | 3 |
| Amaranthaceae | Redroot pigweed (*Amaramthus retroflexus*) | 0 | 0 | 3 | 2 | 2 | 3 | 3 | 2 | 2 | 3 |
| | Alligator weed (*Alternanthera philoxeroides*) | 0 | 0 | 3 | 3 | 2 | 3 | 3 | 4 | 4 | 3 |
| | Pigweed (*Amaranthus spinosus*) | 0 | 0 | 3 | 2 | 2 | 2 | 2 | 3 | 3 | 3 |
| Malvaceae | Malvaceae | 0 | 0 | 3 | 2 | 2 | 2 | 2 | 2 | 2 | 3 |
| | *Abrtilon theophrasti* | 0 | 0 | 2 | 2 | 2 | 3 | 3 | 2 | 3 | 3 |
| Polygonaceae | *Polygonum lapathifolium* | 0 | 0 | 2 | 2 | 2 | 2 | 2 | 2 | 2 | 3 |
| | *Rumex japonicus* | 0 | 0 | 2 | 1 | 2 | 2 | 2 | 3 | 2 | 3 |
| | *Polygonum perfoliatum* | 0 | 0 | 3 | 2 | 2 | 3 | 3 | 3 | 3 | 3 |
| | *Polygonum hydropiper* | 0 | 0 | 3 | 2 | 2 | 3 | 2 | 3 | 3 | 3 |
| | *Rumex dentatus* | 0 | 0 | 2 | 2 | 2 | 2 | 2 | 3 | 3 | 2 |
| Euphorbiaceae | *Acalypha australis* | 0 | 0 | 3 | 2 | 2 | 2 | 3 | 3 | 3 | 2 |
| Cannabinaceae | *Humulus scandens* | 0 | 0 | 3 | 2 | 2 | 3 | 3 | 2 | 3 | 2 |
| Labiatae | *Perilla frutescens* | 0 | 0 | 2 | 2 | 3 | 2 | 2 | 3 | 2 | 2 |
| | *Galeopsis bifida* | 0 | 0 | 3 | 2 | 2 | 2 | 3 | 3 | 2 | 3 |
| | *Lamium amplexicaule* | 0 | 0 | 3 | 2 | 3 | 2 | 3 | 3 | 2 | 2 |
| | *Mosla scabra* | 0 | 0 | 2 | 2 | 2 | 2 | 2 | 2 | 2 | 2 |
| scrophulariaceae | *Veronica didyma* | 0 | 0 | 2 | 3 | 2 | 2 | 2 | 3 | 3 | 3 |
| | *Veronica percica* | 0 | 0 | 3 | 2 | 2 | 2 | 3 | 3 | 3 | 3 |
| commelinaceae | *Commelina communis* | 0 | 0 | 4 | 2 | 2 | 3 | 3 | 2 | 4 | 3 |
| | *Commelina bengalensis* | 0 | 0 | 4 | 3 | 3 | 3 | 3 | 3 | 4 | 3 |
| convolvulaceae | Japanese false bindweed (*Calystegia hederacea*) | 0 | 0 | 4 | 3 | 3 | 4 | 3 | 4 | 4 | 4 |
| | *Dichondra repens* | 0 | 0 | 3 | 2 | 2 | 3 | 3 | 2 | 3 | 2 |
| | *Pharbitis nil* | 0 | 0 | 2 | 2 | 3 | 2 | 2 | 3 | 3 | 3 |
| compositae | *Lapsana apogonoides* | 0 | 0 | 4 | 3 | 2 | 3 | 3 | 3 | 4 | 3 |
| | *Xanthium sibiricum* | 0 | 0 | 3 | 2 | 2 | 2 | 2 | 2 | 3 | 3 |
| | *Conyza canademsis* | 0 | 0 | 4 | 3 | 3 | 3 | 3 | 4 | 4 | 3 |
| | *Eclipta prostrata* | 0 | 0 | 4 | 3 | 4 | 3 | 3 | 4 | 4 | 4 |
| | *Sonchus oleraceus* | 0 | 0 | 4 | 3 | 3 | 3 | 3 | 3 | 4 | 4 |
| | *Aster ageratoides* var. *scaberulus* | 0 | 0 | 4 | 3 | 3 | 4 | 3 | 4 | 4 | 4 |
| | *Youngia japonica* | 0 | 0 | 3 | 3 | 3 | 3 | 3 | 3 | 3 | 4 |
| | *Sonchus asper* | 0 | 0 | 4 | 3 | 3 | 3 | 3 | 3 | 4 | 3 |
| | *Crisium setosum* | 0 | 0 | 3 | 3 | 3 | 3 | 3 | 3 | 4 | 4 |
| | *Erigeron annuus* | 0 | 0 | 3 | 3 | 4 | 3 | 3 | 4 | 4 | 3 |
| | *Ambrosia artemisiifolia* | 0 | 0 | 3 | 3 | 2 | 3 | 3 | 4 | 3 | 3 |
| | *Carpesium abrotanoides* | 0 | 0 | 3 | 2 | 2 | 2 | 3 | 3 | 4 | 2 |
| | *Eupatorium adenophorum* | 0 | 0 | 4 | 3 | 4 | 4 | 4 | 4 | 4 | 4 |
| | *Trifolium pretense* | 0 | 0 | 3 | 3 | 3 | 3 | 3 | 4 | 4 | 4 |
| Rosaceae | *Duchesnea indica* | 0 | 0 | 2 | 2 | 3 | 2 | 2 | 3 | 3 | 3 |
| Vitaceae | *Cayratia japonica* | 0 | 0 | 2 | 2 | 2 | 2 | 2 | 3 | 3 | 3 |
| | *Parthenocissus tricuspidata* | 0 | 0 | 2 | 2 | 3 | 2 | 2 | 3 | 3 | 3 |
| Chenopodiaceae | *Chenopodium serotinum* | 0 | 0 | 3 | 2 | 2 | 2 | 2 | 3 | 3 | 3 |
| Oxalidaceae | *Oxalis corniculata* | 0 | 0 | 4 | 4 | 3 | 4 | 4 | 4 | 4 | 4 |
| Plantaginaceae | *Plantago asiatica* | 0 | 0 | 3 | 2 | 3 | 2 | 3 | 3 | 2 | 2 |
| cyperaecae | *Cyperus rotundus* | 0 | 0 | 2 | 2 | 2 | 2 | 2 | 2 | 2 | 2 |
| | *Cyperus difformis* | 0 | 0 | 4 | 3 | 3 | 3 | 3 | 3 | 4 | 3 |
| | *Fimbristylis miliacea* | 0 | 0 | 3 | 2 | 2 | 3 | 3 | 2 | 3 | 2 |

The results listed in the table 10 suggest that eight compounds (7, 14, 15, 16, 40, 44, 48, and 53) have potential to be used to control or kill grassy weed such as Common crabgrass, Barnyardgrass, Difformed galingale, broadleaf weeds, Yerbadetajo, Copperleaf, Chenopodium serotinum, Commelina communis, Alligator weed, Redroot pigweed, Japanese false bindweed, Sonchus oleraceus etc.

Example 8

Compounds 1, 2, 3, and 40 were dissolved in small amount of methanol and diluted with distilled water to concentration of 50 μg/mL. The solution was sprayed to the soil sample until the soil was wet but not overflows. After standing at room temperature for 3 hours, the soil sample was washed with water and methanol. The wash solution was collected and concentrated. Such process was repeated three times. The concentrated solutions were used for herbicidal activity test using the method of needle puncture on Crofton weed. Methanol water solution and pure water were used as control. The experiment for every sample was repeated six times. The spot diameters were measured with vernier caliper after the plant was kept under natural light at 25° C. for 24 hours (Table 11).

TABLE 11

Evaluation compound toxicity after they were treated with soil

| Treatment | Average diameter of the spot after 24 h (mm) | |
|---|---|---|
|  | H₂O wash | Methanol wash |
| H₂O control | 0.234 ± 0.045 | |
| Methanol control | 0.288 ± 0.024 | |
| 1 | 0.223 ± 0.077 | 0.292 ± 0.041 |
| 2 | 0.280 ± 0.030 | 0.362 ± 0.012 |
| 3 | 0.273 ± 0.062 | 0.334 ± 0.082 |
| 40 | 0.336 ± 0.050 | 0.416 ± 0.024 |

Based on data listed in Table 11, it is clear that the herbicidal activity of all 4 compounds were completely lost after the soil treatment.

What is claimed is:

1. A compound represented by formula (I), or (II), or a salt thereof,

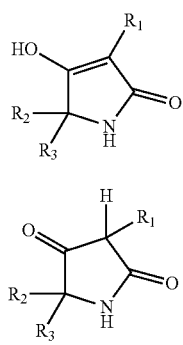

wherein
R$^1$ independently and at each occurrence represents H; or —C$_k$H$_{2k+1}$, —OC$_k$H$_{2k+1}$, —(C═O)C$_k$H$_{2k+1}$, —COOC$_k$H$_{2k+1}$, —C$_k$H$_{2k-1}$, —OC$_k$H$_{2k-1}$, —(C═O)C$_k$H$_{2k-1}$, or —COOC$_k$H$_{2k-1}$, each unsubstituted or substituted by one or more substituents selected from a heterocycle, an aryl, a phenylalkyl, a heterocycloalkyl phenyl, a heterocycloalkyl, a heterocycloalkoxyl, a phenoxyl; a phenoxy phenyl; a halogen, a cyano, a nitro, an alkoxyalkyl, an alkoxycarbonyl, and/or an amido; wherein k represents an integer from 1 to 8;
R$^2$ represents H, CH$_3$— or CH$_3$CH$_2$—; and
R$^3$ represents a straight or branched chain C$_n$H$_{2n+1}$, or C$_n$H$_{2n-1}$ group which is substituted by a halogen group or a cyano group wherein n is an integer from 3 to 15.

2. A compound of claim 1, represented by formula (III), (IV) or (V), or a salt thereof,

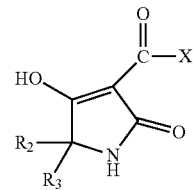

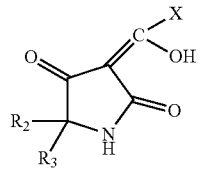

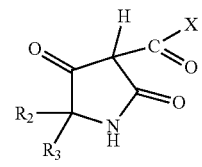

wherein
X independently and at each occurrence represents H; or —C$_m$H$_{2m+1}$, or —OC$_m$H$_{2m+1}$, each unsubstituted or substituted by one or more substituents selected from a heterocyclic alkyl, a heterocyclic aryl, an aryl, a phenylalkyl, a heterocycloalkyl phenyl, a heterocycloalkyl, a heterocycloalkoxyl, a phenoxyl; a phenoxy phenyl; a halogen, a cyano, a nitro, an alkoxyalkyl, an alkoxycarbonyl, and/or an amido;
R$^3$ is a halogen, —CN, a phenyl, a halogenated alkyl, a cyano-alkyl, a phenylalkyl, a halogenoalkenyl, a cyanoalkenyl, or a phenylalkenyl; and
m represents an integer from 1 to 7.

3. A herbicide composition for killing weeds, comprising an effective amount of the compound of claim 1 and a suitable additive.

4. A method of eradicating weeds, the method comprises applying to weeds selected from the group consisting of broadleaf weeds, grassy weeds, and sedge weeds an effective amount of a compound of claim 1, or a salt thereof.

5. A method of eradicating weeds, comprises applying to weeds selected from the group consisting of broadleaf weeds, grassy weeds, and sedge weeds an effective amount of a herbicide composition of claim 3.

6. The method of claim 4, wherein the compound is applied in a solution having a concentration of 10-800 µg of the compound per 1 g of the solution.

7. The method of claim 4, wherein the compound is applied under exposure to sun light.

8. The method of claim 4, wherein the broadleaf weeds are crofton weeds.

* * * * *